(12) United States Patent
Hara et al.

(10) Patent No.: US 6,481,848 B2
(45) Date of Patent: Nov. 19, 2002

(54) OPHTHALMOLOGIC APPARATUS

(75) Inventors: Kunihiko Hara, Tokyo (JP); Yasuhisa Ishikura, Tokyo (JP); Hiroshi Iijima, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 146 days.

(21) Appl. No.: 09/746,101

(22) Filed: Dec. 21, 2000

(65) Prior Publication Data
US 2001/0005260 A1 Jun. 28, 2001

(30) Foreign Application Priority Data
Dec. 22, 1999 (JP) .............................. 11-365092

(51) Int. Cl.[7] .................................................. A61B 3/00
(52) U.S. Cl. ...................................................... 351/245
(58) Field of Search ................................. 351/200, 204, 351/205, 208, 245, 221

(56) References Cited
U.S. PATENT DOCUMENTS 4,139,280 A * 2/1979 Kohler ......................... 351/245
5,488,443 A * 1/1996 Ota et al. .................... 351/221
5,629,747 A * 5/1997 Miyake ....................... 351/245

* cited by examiner

Primary Examiner—George Manuel
(74) Attorney, Agent, or Firm—Chapman and Cutler

(57) ABSTRACT

An ophthalmologic apparatus is disclosed, in which even in the case where the range of lateral relative movement of a trestle is limited with respect to a base, the measurement can be continued without enlarging the space occupied by the apparatus body and without imposing an extra burden on the testee. The apparatus comprises a trestle (4) mounted on a base (3) and laterally movable relative to the base (3) and has a limited range, and a measuring head portion (5) mounted on the trestle (4) and automatically laterally moved relative to the trestle (4) with respect to a reference position (H1). In the case where the trestle (4) moves rightward or leftward and reaches a movement limit position O2, O3, the reference position (H1) of the measuring head portion (5) with respect to the trestle (4) is shifted in the direction in which the trestle (4) moves.

6 Claims, 4 Drawing Sheets

OPHTHALMOLOGIC APPARATUS

BACKGROUND OF THE INVENTION

1. Field of the Invention

The present invention relates to an improved ophthalmologic apparatus comprising a trestle mounted on a base and laterally movable relatively to the base within a limited range and a measuring head unit mounted on the trestle and movable automatically relatively to the trestle in lateral direction with respect to a reference position within a predetermined range.

2. Description of the Related Art

An ophthalmologic apparatus such as a tonometer is known to comprise a trestle mounted on a base and laterally movable relatively to the base within a limited range and a measuring head unit mounted on the trestle and movable automatically relatively to the trestle in lateral direction with respect to a reference position within a predetermined range.

In such an apparatus as described above, rough alignment is carried out by moving the trestle longitudinally and laterally with respect to the base. When the eye to be inspected enters an auto alignment range, the measuring head portion is driven automatically in a predetermined range with respect to a reference position, thus making it possible to execute the measurement of the intra-ocular pressure automatically.

In the conventional ophthalmologic measuring instrument, however, the lateral relative travel range of the trestle is so limited that even when the trestle is moved laterally in full, the measuring head portion often fails to enter the auto alignment range and the measurement is impossible.

This situation occurs, for example, in the case where the face of the testee is not rightly directed toward the apparatus, In such a case, the testee is inconveniently instructed to direct his face rightly toward the apparatus. Also, the measurement may be impossible in the case where the width of the eye of the is too large.

A solution conceived to solve this problem is to enlarge the lateral relative travel range of the trestle with respect to the base. This configuration, if employed, would undesirably increase the space occupied by the ophthalmologic apparatus.

SUMMARY OF THE INVENTION

The present invention has been developed in view of this situation, and the object thereof is to provide an ophthalmologic apparatus in which even in the case where the lateral relative travel range of the trestle with respect to the base is limited, the measurement can be continued without enlarging the space occupied by the apparatus body and also without imposing an extra burden on the testee.

According to a first aspect of the invention, there is provided an ophthalmologic apparatus comprising a trestle mounted on a base and laterally movable relatively to the base with respect to a reference position within a limited range of relative movement, and a measuring head portion mounted on the trestle and automatically moved relatively to the trestle with respect to a reference position within a predetermined range, wherein when the trestle is moved in right or left direction and comes to be located at a movement limit position, the reference position of the measuring head portion with respect to the trestle is shifted in the direction in which the trestle moves.

According to a second aspect of the invention, there is provided an ophthalmologic apparatus comprising a trestle mounted on a base and laterally movable relatively to the base within a limited range of relative movement, a measuring head portion mounted on the trestle and automatically moved relatively to the trestle with respect to a reference position within a predetermined range in lateral direction, and a left/right decision switch for deciding which eye of right or left is to be measured, by laterally moving the trestle, wherein in the case where the left/right decision switch decides that the left eye is to be measured, the reference position of the measuring head portion with respect to the trestle is shifted leftward as viewed from the testee, while in the case where the left/right decision switch decides that the right eye is to be measured, the reference position of the measuring head portion with respect to the trestle is shifted rightward as viewed from the testee.

According to a third aspect of the invention, there is provided an ophthalmologic apparatus further comprising an announcing means for informing the testee that the reference position of the measuring head portion is shifted in the direction of movement of the trestle.

According to a fourth aspect of the invention, there is provided an ophthalmologic apparatus, wherein before the reference position of the measuring head portion is shifted relatively to the trestle in the direction of movement of the trestle, the head measuring unit is driven once in the direction away from the eye to be measured.

According to a fifth aspect of the invention, there is provided an ophthalmologic apparatus wherein in the case where the trestle is located at the movement limit position, the inspector is warned of the fact.

According to a sixth aspect of the invention, there is provided an ophthalmologic apparatus comprising a trestle mounted on a base and laterally movable relatively to the base within a limited range of relative movement, a measuring head portion mounted on the trestle and automatically moved relatively to the trestle within a predetermined lateral range with respect to a reference position, and a moving direction detection means for detecting the direction of movement of the trestle, wherein in the case where the moving direction detection means detects that the trestle moves leftward, the reference position of the measuring head portion with respect to the trestle is shifted leftward, while in the case where the movement direction detection means detects that the trestle moves rightward, the reference position of the measuring head portion with respect to the trestle is shifted rightward.

DESCRIPTION OF THE PREFERRED EMBODIMENTS

First Embodiment of the Invention

Figure 1:
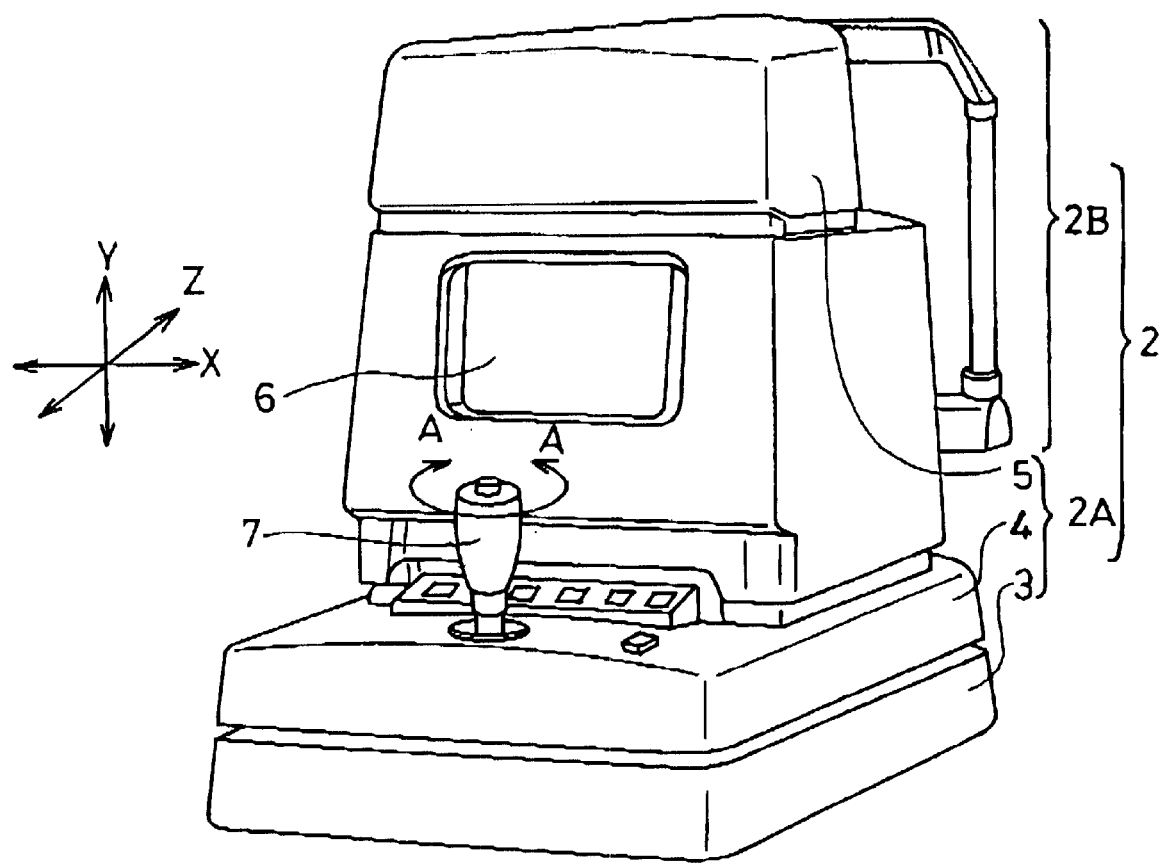
FIG. 1 is a perspective view of an ophthalmologic apparatus according to the present invention.
Figure 2:
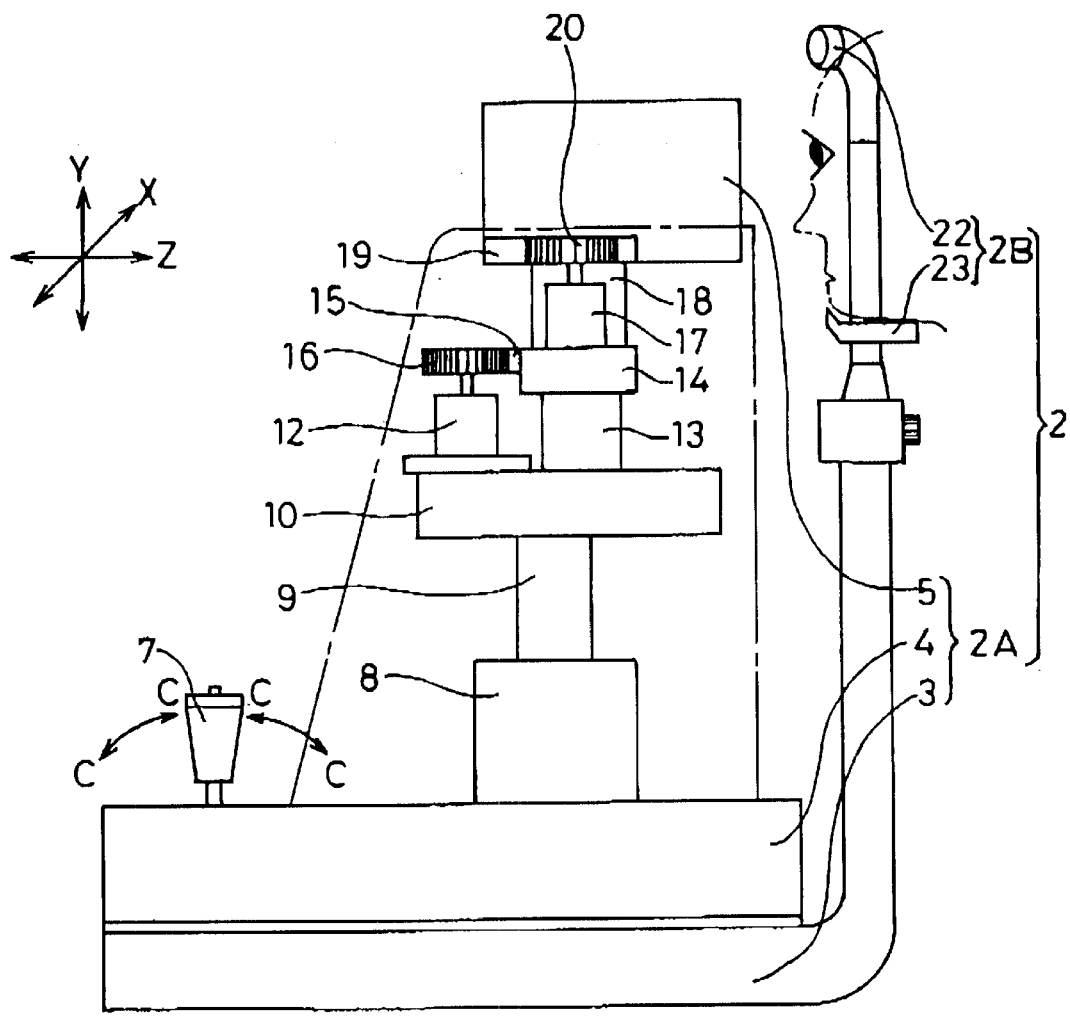
FIG. 2 is a schematic diagram showing the internal structure of the ophthalmologic apparatus shown in FIG. 1.
Figure 3:
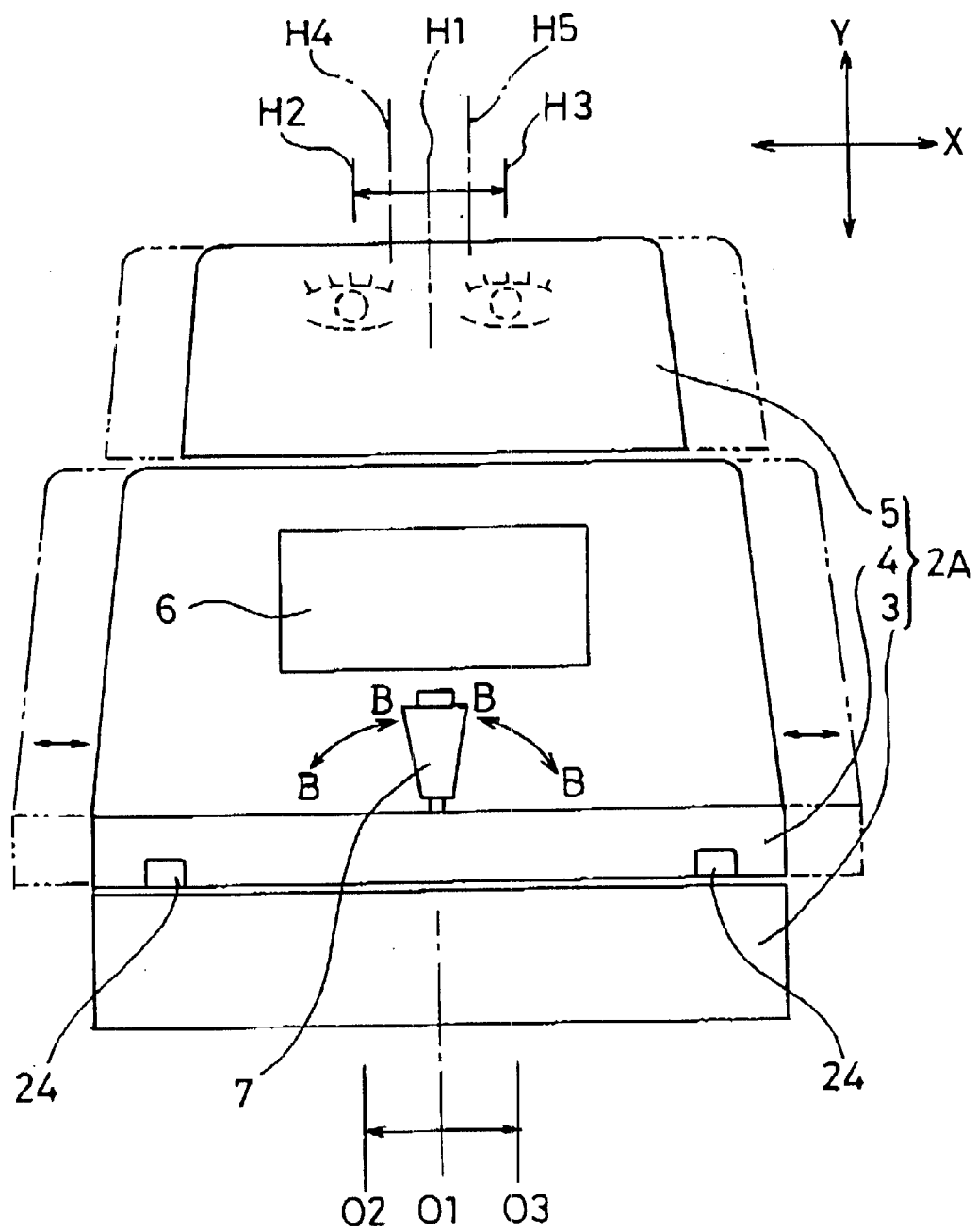
FIG. 3 is a front view of an ophthalmologic apparatus according to the invention as taken from the inspector.

In FIGS. 1 to 3, reference numeral 1 designates a non-contact tonometer constituting an ophthalmologic apparatus. This non-contact tonometer generally comprises an apparatus body 2A and a face receiving member 2B.

The apparatus body 2A includes a base 3, a trestle 4 and a measuring head 5. A display unit 6 and a control lever 7 are arranged on the back of the trestle 4. The measuring head portion 5 includes a well-known optical system for aligning the eye to be inspected and an air pulse jet means (nut shown).

The trestle 4 is movable relatively to the base 3 in longitudinal direction (Z direction) and lateral direction (X direction). A measuring head vertical drive motor 8 for driving the measuring head portion 5 vertically (Y direction) is mounted on the trestle 4. The output shaft 9 of the measuring head vertical drive motor 8 has a table 10 thereon, which in turn has arranged thereon a measuring head lateral drive motor 12 for moving the measuring head portion 5 laterally and a table 13. The table 13 has arranged thereon a slide table 14 which is slidable laterally.

The slide table 14 is formed with a rack 15. A pinion 16 is mounted on the output shaft of the measuring head lateral drive motor 12 and adapted to engage the rack 15 thereby to slide the table 14 laterally.

A measuring head longitudinal drive motor 17 for moving the measuring head portion 5 in longitudinal direction and a table 18 are mounted on the slide table 14. The measuring head portion 5 is mounted on the table 18 slidably longitudinally. The measuring head portion 5 is formed with a rack 19, and a pinion 20 is mounted on the output shaft of the measuring head longitudinal drive motor 17. The pinion 20 and the rack 19 are adapted to engage each other thereby to slide the measuring head portion 5 longitudinally.

Figure 4:
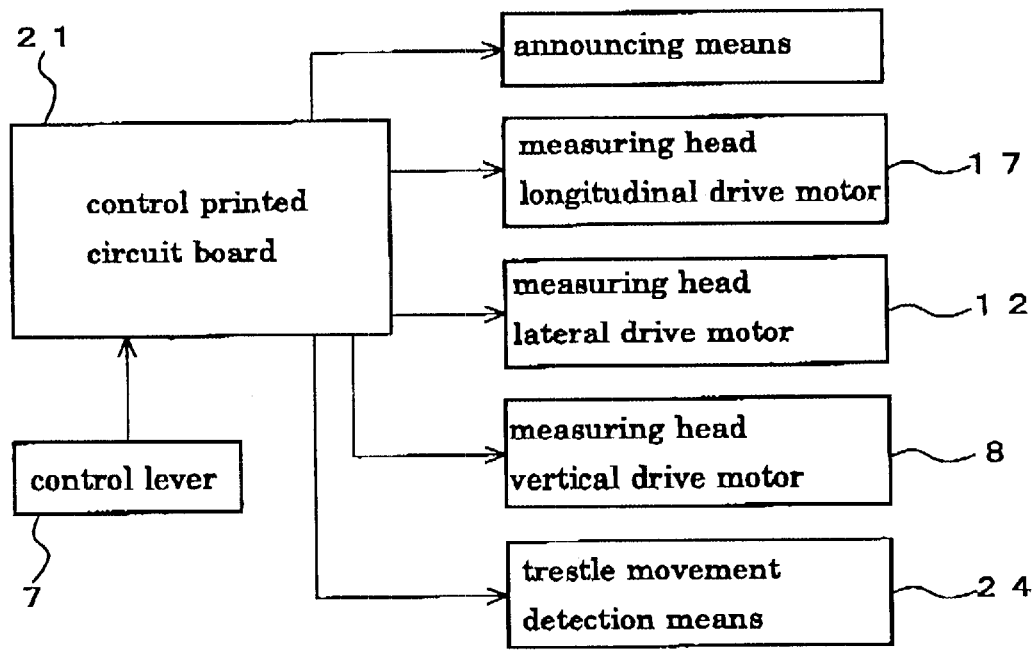
FIG. 4 is a block diagram showing a control circuit of the ophthalmologic apparatus according to the invention.

The apparatus body 2A includes a control printed circuit board 21 shown in FIG. 4. The control printed circuit board 21 detects the rotational operation (in the direction of arrow A—A in FIG. 1) of the control lever 7, and drives the measuring head vertical drive motor 8. The trestle 4 is moved laterally with respect to the base 3 by the lateral tilt operation (in the direction of arrow B—B in FIG. 3) of the control lever 7, and the trestle 4 is moved longitudinally with respect to the base 3 by the longitudinal tilt operation (in the direction of arrow C—C in FIG. 2) of the control lever 7.

Trestle movement limiting means 24, 24 for limiting the lateral movement of the trestle 4 are arranged on the trestle 4. The trestle 4 is movable in two lateral directions within the range defined by limit positions 02, 03 about the reference position H1, as shown in FIG. 3. The measuring head portion 5, as shown in FIG. 3, is automatically reciprocated laterally within the range (auto alignment range) defined by limit positions H2, H3 about the reference position H1.

The face receiving member 2B generally includes a chin rest 22 and a forehead support 23. The intra-ocular pressure is measured for the testee who has fixed his face on the apparatus body 2.

When measuring the eye E of the testee, the trestle 4 is manually moved both longitudinally and laterally, while at the same time moving the measuring head portion 5 vertically by rotating the control lever 7 thereby to roughly align the apparatus body with respect to the testee. Upon complete rough alignment, the position of the measuring head portion 5 relative to the eye E to be inspected is detected by the alignment optical system. Thus, the measuring head portion 5 is driven automatically in longitudinally, laterally and vertically for automatic measurement.

Depending on the testee, the rough alignment is impossible even in the case where the trestle 4 is moved leftward or rightward in full. In such a case, upon detection by the trestle movement limit detection means 24, 24 that the trestle 4 has reached the movement limit position, the control printed circuit board 21 shifts the measuring head portion 5 from the reference position H1 to the reference position H4 or the reference position H5 with respect to the trestle 4.

The trestle movement limit detection means 24 is a reflection-type photo-interruptor, a microswitch or the like for detecting that the trestle 4 has moved laterally from the base 3 and the trestle movement detection means 24 has come off from the surface of the base 3.

Specifically, in the case where the trestle 4 is moved to the extreme left and has reached the movement limit position in order to measure the right eye to be inspected, the reference position H1 of the measuring head portion 5 is shifted to the reference position H4 thereby to drive the measuring head portion 5 automatically, whereas in the case where the trestle 4 is moved to the extreme right and has reached the movement limit position in order to measure the left eye to be inspected, the reference position H1 of the measuring head portion 5 is shifted to the reference position H5 thereby to drive the measuring head portion 5 automatically. Before changing the reference position, it is desirable to retreat the measuring head portion 5 temporarily to permit the reference position to be changed while avoiding the contact of the measuring head portion 5 with the face of the testee positively.

At the same time, the control printed circuit board 21 informs the inspector that the reference position of the measuring head portion 5 has been changed. A display unit 6 is used, for example, as this announcing means.

With this configuration, measurement can be carried out in such a manner that the face of the testee is rightly directed to the apparatus body without changing the face position of the testee.

The first embodiment of the invention is so configured that the inspector is informed that the reference position of the measuring head portion 5 has been changed. As an alternative, the inspector may be informed that the measuring head portion 5 has reached the movement limit position.

Second Embodiment of the Invention

Figure 5:
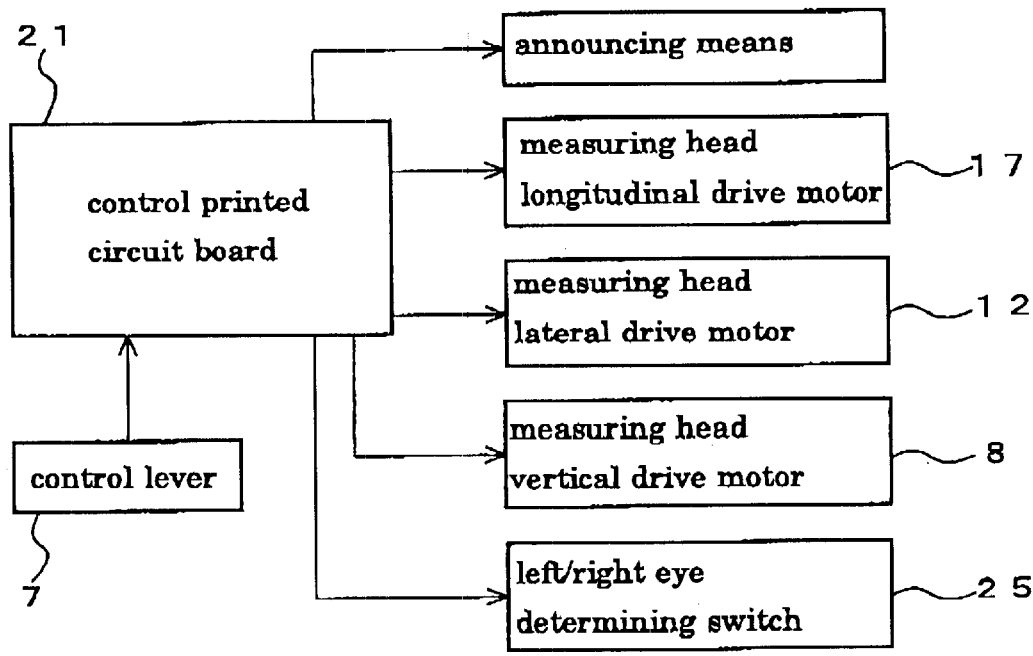
FIG. 5 is a block diagram showing another example of the control circuit of the ophthalmologic apparatus according to the invention.

FIG. 5 is a diagram for explaining a second embodiment of the invention. In the second embodiment, instead of the trestle 4 changing the reference position of the measuring head portion 5 by detecting the movement limit position, the apparatus body 2A includes a left/right eye determining switch 25 for determining which eye is to be measured, left eye or right eye, and the reference position of the measuring head portion 5 is changed by the left/right eye determining switch 25.

Embodiments of the invention have been explained above. Apart from these embodiments, the reference position of the measuring head portion 5 may be shifted by detecting the direction in which the trestle 4 moves.

According to the present invention, even in the case where the range of lateral movement of the trestle relative to the base is limited, the measurement can be continued without enlarging the space occupied by the apparatus body and without imposing a useless burden on the testee, thereby increasing the speed of measurement.

What is claimed is:

1. An ophthalmologic apparatus comprising a trestle mounted on a base and laterally movable relatively to the base within a limited range of relative movement, and a measuring head portion mounted on the trestle and automatically moved relatively to the trestle with respect to a reference position within a predetermined range in lateral direction, wherein in the case where the trestle is moved in right or left direction and comes to be located at a movement limit position, the reference position of the measuring head portion with respect to the trestle is shifted in the direction in which the trestle moves.

2. An ophthalmologic apparatus comprising a trestle mounted on a base and laterally movable relatively to the base within a limited range of relative movement, and a measuring head portion mounted on the trestle and automatically moved relatively to the trestle with respect to a reference position within a predetermined range in lateral direction, said apparatus further comprising a left/right decision switch for deciding which eye of right or left is to be measured, with the lateral movement of the trestle, wherein in the case where the left/right decision switch decides that the left eye is to be measured, the reference position of the measuring head portion with respect to the trestle is shifted leftward as viewed from the testee, while in the case where the left/right decision switch decides that the right eye is to be measured, the reference position of the measuring head portion with respect to the trestle is shifted rightward as viewed from the testee.

3. An ophthalmologic apparatus according to claim 1, further comprising an announcing means for informing the inspector that the reference position of the measuring head portion is shifted in the direction of movement of the trestle with respect to the trestle.

4. An ophthalmologic apparatus according to claim 1, wherein before the reference position of the measuring head portion is shifted in the direction of movement of the trestle with respect to the trestle, the head measuring unit is driven once in the direction away from the eye to be measured.

5. An ophthalmologic apparatus according to claim 1, wherein in the case where the trestle is located at the movement limit position, the inspector is informed of the fact.

6. An ophthalmologic apparatus comprising a trestle mounted on a base and laterally movable relatively to the base within a limited range of relative movement, and a measuring head portion mounted on the trestle and automatically moved relatively to the trestle with respect to a reference position within a predetermined range in lateral direction, said apparatus further comprising a movement direction detection means for detecting the direction of movement of the trestle, wherein in the case where the movement direction detection means detects that the trestle moves leftward, the reference position of the measuring head portion with respect to the trestle is shifted leftward, while in the case where the movement direction detection means detects that the trestle moves rightward, the reference position of the measuring head portion with respect to the trestle is shifted rightward.

* * * * *